United States Patent [19]

de Araûjo

[11] Patent Number: 5,449,516
[45] Date of Patent: Sep. 12, 1995

[54] BRAZILIAN GINSENG DERIVATIVES FOR TREATMENT OF SICKLE CELL SYMPTOMATOLOGY

[75] Inventor: João T. de Araûjo, Sao Paulo, Brazil

[73] Assignee: Instituto de Medicina Tropical de Sao Paulo, Sao Paulo, Brazil

[21] Appl. No.: 105,745

[22] Filed: Aug. 12, 1993

[51] Int. Cl.⁶ .............................................. A61K 35/78
[52] U.S. Cl. .................................. 424/195.1; 514/25
[58] Field of Search ................... 424/195.1; 514/25

[56] References Cited

U.S. PATENT DOCUMENTS 5,198,225  3/1993  Meghack et al. ................... 424/450

FOREIGN PATENT DOCUMENTS 59-10548  1/1984  Japan ........................... C07C 62/32

OTHER PUBLICATIONS

Nishimoto et al; Phytochemistry 23(1):139–142 (1984).
De Oliveira, et al, Chem. Abst. 96(8):57621q; 1980.
Takemoto et al., Chem. Abst. 99(7):50248b, 1983.
Chem. Abst. 188(23):189046s, 1984.
Nishimoto et al, Chem. Abst. 101(3) 20525q; 1984.

*Primary Examiner*—John W. Rollins
*Attorney, Agent, or Firm*—Brooks Haidt Haffner & Delahunty

[57] ABSTRACT

A process for extracting and isolating compounds from the Brazilian ginseng plant, particularly of the genus Pfaffia and most particularly *Pfaffia paniculata*, results in therapeutic compositions for treatment of sickle cell symptomatology. The extracted compositions are made by crushing the Brazilian ginseng roots, washing the crushed roots in hot alcohol, and then drying and grinding the roots into a powder. The powder is then treated using N-butanol and chromatography to extract the therapeutic compositions. Administration of a therapeutically-effective amount of the Brazilian ginseng compositions to subjects having sickle cell disease symptoms results in increased hemoglobin levels, inhibited red blood cell sickling and generally improved physical condition during the treatment.

5 Claims, No Drawings

BRAZILIAN GINSENG DERIVATIVES FOR TREATMENT OF SICKLE CELL SYMPTOMATOLOGY

BACKGROUND OF THE INVENTION

1. Field of the Invention

The present invention relates generally to therapeutic products and methods for treatment of sickle cell anemia and its symptomatology, and more specifically to a process for the extraction and isolation of therapeutic compositions from the roots of Brazilian ginseng, particularly *Pfaffia paniculata*, and the uses thereof.

2. Description of the Related Art

The root of the plant commonly referred to as "Brazilian Ginseng" and more particularly *Pfaffia paniculata*, has been used as a tonic, aphrodisiac, tranquilizer and folk medicine for centuries. Brazilian ginseng is a perennial wild plant in the Amaranthaceae family and grows primarily within the Goiás region of Brazil. Several pfaffic compounds have been isolated from the roots of Brazilian ginseng, including Pfaffic acid $C_{29}H_{44}O_3$, also known as 3 beta-hydroxy-16, 20-cyclo-30-norolean-12-en-28 oic acid, and various derivatives, including Pfaffosides, which include $C_{40}H_{60}O_{13}$, $C_{46}H_{70}O_{18}$, $C_{41}H_{62}O_{14}$, $C_{50}H_{70}O_{18}$, $C_{47}H_{72}O_{18}$ and $C_{35}H_{52}O_9$, and various saponins.

Japanese Laid-open Patent Application No. SHO 59-10548 describes the extraction of Pfaffic acid, as well as alkyl and acyl derivatives thereof, from Brazilian ginseng. The reference acknowledges the long use of Brazilian ginseng as an Indian folk medicine for treating a variety of ailments: diabetes, ulcers, leukemia and cancers. The reference also describes antioncogenic (anti-neoplasm) agents in Pfaffic acid which inhibit tumor growth. Japanese Application No. SHO 57-118872 similarly describes antioncogenic properties of Brazilian gingseng compounds.

The references, however, fail to discuss the sickle cell symptomatology inhibiting properties of Brazilian ginseng and its derivatives, as described in the present invention. Sickle cell disease or anemia is an inherited chronic anemia in which a large proportion of the normally biconcave, disc-shaped red blood cells sickle, i.e. form a crescent shape, which is not conducive to normal circulatory blood flow, especially through narrow capillary vessels. Persons suffering from sickle cell disease are subject to a wide variety of symptoms and disorders: ulcerations, jaundice, pneumonias, abdominal, leg and skeletal muscle pain, vessel occlusion, and other harmful symptomatology characteristic of sickle cell disease.

It is therefore one object of the present invention to develop a process for extracting and isolating therapeutic products from Brazilian ginseng for the treatment of sickle cell symptomatology.

Another object of the invention is to provide methods for using the extracted, therapeutic Brazilian ginseng products to inhibit the deleterious symptoms of sickle cell disease.

SUMMARY OF THE INVENTION

The present invention is a process for extracting and isolating therapeutic compositions for the treatment of sickle cell symptomatology from the roots of the Brazilian ginseng plant, particularly of the genus Pfaffia and most particularly *Pfaffia paniculata*. The compositions are made by crushing the roots of the Brazilian ginseng, washing the crushed roots in hot alcohol, then drying them and finally grinding them up into a powder. The powder is then treated using N-butanol and chromatography to make a therapeutic Brazilian ginseng powder extract.

The present invention is further directed to the therapeutic use of the Brazilian ginseng powder extract in the treatment of sickle cell symptomatology. Administration of the Brazilian ginseng powder extract to subjects suffering from sickle cell symptomatology resulted in increased hemoglobin levels, inhibited sickling of red blood cells and generally improved physical condition for the duration of the treatment period.

DETAILED DESCRIPTION OF THE PRESENT INVENTION

Although Brazilian ginseng has been used by Brazilian Indians for centuries as a folk medicine, the therapeutic properties of Brazilian ginseng, particularly of the genus Pfaffia and most particularly *Pfaffia paniculata*, powder extracts in treating the symptoms of sickle cell disease have only recently been discovered by the present inventor. The process for extracting and purifying Brazilian ginseng powder, and clinical and laboratory studies of its therapeutic use on subject patients is described below.

Preparation and Purification of the Brazilian Ginseng Powder Extract

Although the entire Brazilian ginseng plant has therapeutic properties, the roots are the best source in obtaining a therapeutic powder extract. After harvesting several Brazilian ginseng roots, the roots are washed in water, preferably by a high-pressure water jet, to remove earth and other adhering foreign substances. Each root is then inspected and all re-entering spots, "wound" spots and adventitious roots are removed.

The roots are then placed in a rotatable drum with running water for a period of approximately two hours during which the roots are further cleansed by means of friction action against one another. The cleaned roots are then crushed or otherwise disaggregated in a clay disaggregator and immediately dried in a heated air oven. After drying for approximately 24–48 hours, the remaining material is powderized in a mill and then treated with either hot methanol or ethanol. After removing all of the debris by decantation, a yellowish powder remains which may be collected and packed in plastic bags.

The yellowish powder is then partitioned in a water-/alcohol mixture, such as a distilled water/N-butanol mixture, and the N-butanol layer of the mixture forms a water insoluble portion and a water soluble portion. Since Pfaffic acid is found in both the water insoluble and soluble portions of the N-butanol layer, both portions are treated to extract the Pfaffic acid and any pfaffic derivatives therein, e.g., Pfaffosides and saponins. Isolation of the insoluble portion of the Pfaffic acid in the water insoluble portion is done by chromatography on silica gel, yielding a powder comprising not only Pfaffic acid but related saponins derived from Pfaffic acid. The water soluble portion of the N-butanol layer is hydrolyzed in an appropriate manner and isolated by silica gel chromatography, yielding a powder comprising Pfaffic acid. The powders are combined to make the Brazilian ginseng powder extract of the invention.

In Vitro Experimentation

This experiment demonstrated both the sickling inhibition and desickling properties of the Brazilian ginseng, particularly *Pfaffia paniculata*, powder extract. In the experiment, blood samples from both sickle cell patients and a control group of normal patients were taken approximately 1-4 hours before the start of laboratory testing. The blood samples were either tested immediately or after being washed three times with a normal saline solution (NaCl 0.9%). Deoxygenation of tested red blood cells was obtained by using a 2% solution of sodium methabisulphite (0.2 g in 10 ml), which causes red blood cells to deoxygenate and sickle.

In an experiment to test the sickling inhibitory properties of the Brazilian ginseng powder extract of the present invention, two 20 microliter blood samples were prepared, one containing red blood cells from a sickle cell patient and a second, control sample of normal red blood cells. Each sample was poured into a test tube. Twenty microliters of a Brazilian ginseng solution was then added to each test tube. The Brazilian ginseng solution used in this experiment was prepared by adding 5 g of the Brazilian ginseng powder extract in a vial of distilled water, stirring the contents, letting the mixture sit for 10 days, and then centrifuging the mixture. The floating yellowish liquid at the top was then concentrated and used in the present experiment.

The test tubes containing the mixture of Brazilian ginseng solution with either normal or sickled blood cells were then gently stirred, and samples of each were dropwise placed on a microscope slide and then covered and sealed with paraffin to prevent oxygen contamination to the sample. Microscope readings were then made at 6 hour intervals, i.e. 6, 12, 18 and 24 hours.

After 18 hours it was observed that the sickled cells had desickled, i.e. changed to the biconcave disc-shape of normal red blood cells. The Brazilian ginseng solution had thus corrected the abnormal sickle or crescent cell shape.

In another experiment to test the desickling properties of the extracted Brazilian ginseng, particularly *Pfaffia paniculata*, compositions a 0.5 ml blood sample of normal red blood cells was placed into a test tube along with an equal measure of methabisulphite, and the mixture gently stirred and then covered by a layer of oil to prevent contact with air. After one or two hours, the methabisulphite caused the normally disc-shaped blood cells to become deoxygenated and they sickled. Desickling was then achieved by mixing one drop of the now sickled red blood cells on a microscope slide with a drop of the Brazilian ginseng solution described above. The mixture was then covered with a microscope slide and sealed along the edges with paraffin. As before, microscopic readings were made at 6 hour intervals.

As with the first test tube, after 18 hours the sickled cells had reverted to their normal shape, and had apparently become oxygenated as well.

Toxicity Experimentation

For a period of thirty days, two groups of rats were studied to determine if the Brazilian ginseng, particularly *Pfaffia paniculata*, powder extract was toxic. A first group of rats was fed a normal ration, and a second group a ration containing equal parts of Brazilian ginseng powder extract and the normal ration. No abnormal behavior was observed in either group for the duration of the study. After the thirty days, the rats were sacrificed for autopsy analysis. Macroscopic and microscopic studies of the hearts, lungs, brains, livers, spleens, intestines and kidneys of the rats in both groups did not reveal any lesions or other signs of toxicity.

In light of the use of Brazilian ginseng by Indians for several centuries, the toxicity of Pfaffic acid in humans is apparently low. As noted by Japanese Laid-Open Application No. SWO 59-10548, large dosages of from 1-1.5 grams of Brazilian ginseng per day per patient resulted in no side effects, and simple derivatives of Pfaffic acid, e.g. alkyl and acyl Pfaffic acids, should exhibit the same low toxicity levels. The Brazilian ginseng powder extract of the present invention was taken for a period of over three years by several patients and researchers without any secondary effects.

Clinical Trials

Thirty patients suffering from the effects of sickle cell disease were studied in a randomized double-blind clinical trial. One half of the patients were given orally two 500 mg capsules of a powder extract of *Pfaffia paniculata* every 8 hours. The other group was given orally two placebos at the same intervals. The placebos were prepared using capsules and liquids having the same appearance as the *Pfaffia paniculata* powder extract. Some of the patients in both groups were children who were given the *Pfaffia paniculata* powder extract dissolved in water at a concentration of approximately 250 mg per 5 ml of water.

All of the patients in the study had a prior history of frequent abdominal, leg and skeletal pain, which was due to blood vessel occlusions, and other sickle cell symptomatology. Almost one half of the patients exhibited jaundice, three had leg ulcerations, and some had required blood transfusions. Tables 1 and 2 show hematological studies of the two groups of patients prior to treatment. The patients in the first group, listed in Table 1, were given the *Pfaffia paniculata* powder extract capsules, and the patients in the second or control group, listed in Table 2, received the placebos. Of the fifteen patients treated with *Pfaffia paniculata* powder extract, five were male and the average age of the group was 14. In the control group, six were male and the average age was 15.

Hematological studies of the group treated with the *Pfaffia paniculata* powder extract and the control group after three months are shown in Tables 3 and 4, respectively.. As listed in Table 3, the hemoglobin (HB) levels for most of the patients in the group treated with *Pfaffia paniculata* powder extract increased to 8-9 g/dL, hematocrit (HT) levels increased, and the number of peripheral erythrocytes (fetal hemoglobin) decreased, indicating desickling. Clinically, the group treated with *Pfaffia paniculata* powder extract exhibited increased mental and physical activity, had less pain, and needed no blood transfusions, as compared to themselves before treatment and as compared to the control group in Table 4. The group members' physical appearance also improved. Although there was one incidence of pneumonia among the group treated with the *Pfaffia paniculata* powder extract, the individual in question had had seven bouts of pneumonia in the year prior to treatment despite taking penicillin. Further, incidences of jaundice, lower limb ulcerations, priapism, thromboembolisms, chest-syndromes and other ailments within the group decreased.

Comparison of the laboratory data from the non-treated group at three months, Table 4, with the pretreatment data in Table 2, shows no significant changes in hemoglobin levels or fetal hemoglobin. Also, the control group subjects continued to suffer from various ailments, including 2-3 bouts of pneumonia per year and frequent thromboembolisims.

Tables 5 and 6 show the results of hematological studies of the group treated with the *Pfaffia paniculata* powder extract and the control group, respectively, one year after terminating the study and the *Pfaffia paniculata* treatments. In general, within three to six months after terminating treatment all of the patients in the treated group reverted to their pretreatment clinical condition and all of the sickle cell symptomatology reappeared: decreased hemoglobin levels, increased pain, jaundice, etc. One of the patients treated with the *Pfaffia paniculata* powder extract was later retreated and showed improvement in his clinical condition. Other patients given Brazilian ginseng or *Pfaffia paniculata* powder extract capsules over a period of three years required no blood transfusions, maintained their physical appearance, and did not develop the wide panoply of physical ailments typical of sickle cell disease.

Analysis of the clinical and laboratory evidence clearly shows measurable improvement in those sickle cell patients treated with Brazilian ginseng powder extract. Laboratory evidence also suggests that at least two or three of the six known Pfaffosides may be responsible for many beneficial effects of the Brazilian ginseng powder extract, which include reduction in pneumonias, vessel-occlusive crises and many other side-effects of sickle cell disease, as well as better life quality for the patients.

It should be understood that Brazilian ginseng extract or capsules made thereof can include a carrier and/or be coated with a conventional excipient material, allowing transportation and release of the therapeutic extract at a specific location along the alimentary tract. It should also be understood that the carrier and/or excipient may be admixed with the extract.

TABLE 1

| CASE NO. | ERYTROCYTES mm$^3$ | HB g/dL | HT % | MCV fL | MCH pg | MCHC g/dL | RETICULOCYTES % | SICKLE CELL/ 1000 | PERIPHERAL ERYTROBLAST IN 100 CELLS |
|---|---|---|---|---|---|---|---|---|---|
| 01 | 2,300,000 | 6.5 | 21 | 91 | 28 | 30 | 26 | 70 | 08 |
| 02 | 2,496,000 | 6.7 | 21 | 90 | 28 | 31 | 27 | 80 | 09 |
| 03 | 2,650,000 | 7.0 | 23 | 86 | 30 | 26 | 26 | 100 | 12 |
| 04 | 2,760,000 | 7.5 | 24 | 86 | 31 | 27 | 24 | 180 | 06 |
| 05 | 2,166,000 | 6.4 | 19 | 90 | 30 | 33 | 18 | 150 | 10 |
| 06 | 2,286,000 | 6.5 | 19 | 89 | 30 | 33 | 17 | 160 | 07 |
| 07 | 2,360,000 | 6.8 | 21 | 91 | 29 | 32 | 25 | 100 | 06 |
| 08 | 2,356,000 | 7.0 | 21 | 90 | 29 | 32 | 26 | 130 | 07 |
| 09 | 3,280,000 | 8.4 | 29 | 90 | 26 | 28 | 15 | 25 | 06 |
| 10 | 2,650,000 | 7.8 | 25 | 96 | 30 | 31 | 14 | 180 | 06 |
| 11 | 2,960,000 | 8.0 | 26 | 92 | 27 | 30 | 20 | 130 | 03 |
| 12 | 2,760,000 | 8.2 | 25 | 92 | 30 | 32 | 10 | 80 | 02 |
| 13 | 2,660,000 | 8.3 | 24 | 92 | 31 | 34 | 09 | 200 | 02 |
| 14 | 2,780,000 | 8.5 | 25 | 92 | 31 | 34 | 12 | 150 | 00 |
| 15 | 2,770,000 | 8.6 | 26 | 96 | 31 | 33 | 08 | 200 | 00 |

TABLE 2

| CASE NO. | ERYTROCYTES mm$^3$ | HB g/dL | HT % | MCV fL | MCH pg | MCHC g/dL | RETICULOCYTES % | SICKLE CELL/ 1000 | PERIPHERAL ERYTROBLAST IN 100 CELLS |
|---|---|---|---|---|---|---|---|---|---|
| 01 | 2,460,000 | 6.7 | 21 | 87 | 27 | 32 | 15 | 160 | 06 |
| 02 | 2,480,000 | 7.0 | 22 | 91 | 29 | 31 | 16 | 80 | 08 |
| 03 | 3,000,000 | 8.0 | 27 | 90 | 26 | 30 | 08 | 100 | 06 |
| 04 | 3,260,000 | 8.1 | 26 | 81 | 25 | 31 | 04 | 60 | 02 |
| 05 | 3,260,000 | 8.3 | 30 | 93 | 26 | 28 | 10 | 80 | 03 |
| 06 | 2,760,000 | 8.2 | 25 | 92 | 30 | 33 | 14 | 100 | 04 |
| 07 | 2,650,000 | 7.2 | 23 | 88 | 27 | 31 | 16 | 120 | 05 |
| 08 | 2,760,000 | 7.5 | 24 | 88 | 28 | 31 | 08 | 126 | 04 |
| 09 | 2,850,000 | 9.1 | 25 | 89 | 32 | 36 | 15 | 90 | 03 |
| 10 | 3,100,000 | 9.2 | 28 | 90 | 29 | 33 | 16 | 92 | 02 |
| 11 | 2,860,000 | 8.9 | 26 | 92 | 32 | 37 | 12 | 100 | 04 |
| 12 | 2,650,000 | 8.3 | 24 | 92 | 32 | 34 | 16 | 110 | 05 |
| 13 | 2,450,000 | 7.2 | 21 | 87 | 30 | 34 | 20 | 160 | 06 |
| 14 | 3,310,000 | 8.6 | 29 | 87 | 26 | 29 | 18 | 90 | 03 |
| 15 | 3,260,000 | 9.2 | 28 | 87 | 29 | 32 | 17 | 90 | 04 | hemoglobin levels between 8 and 9 g/dL, improved

TABLE 3

| CASE NO. | ERYTROCYTES mm$^3$ | HB g/dL | HT % | MCV fL | MCH pg | MCHC g/dL | RETICULOCYTES % | SICKLE CELL/ 1000 | PERIPHERAL ERYTROBLAST IN 100 CELLS |
|---|---|---|---|---|---|---|---|---|---|
| 01 | 2,700,000 | 7.8 | 25 | 92 | 28 | 32 | 10 | 50 | 02 |
| 02 | 2,260,000 | 7.0 | 21 | 95 | 31 | 33 | 15 | 180 | 04 |
| 03 | 3,159,000 | 9.0 | 29 | 93 | 29 | 31 | 08 | 60 | 00 |
| 04 | 2,644,000 | 8.3 | 24 | 92 | 31 | 34 | 11 | 100 | 04 |
| 05 | 2,865,000 | 8.4 | 26 | 92 | 31 | 34 | 08 | 50 | 01 |
| 06 | 3,196,000 | 9.9 | 28 | 90 | 31 | 35 | 10 | 90 | 03 |
| 07 | 3,096,000 | 8.1 | 25 | 83 | 27 | 32 | 23 | 40 | 04 |
| 08 | 2,890,000 | 9.5 | 27 | 96 | 33 | 35 | 07 | 55 | 01 |

TABLE 3-continued

| CASE NO. | ERYTROCYTES mm³ | HB g/dL | HT % | MCV fL | MCH pg | MCHC g/dL | RETICULOCYTES % | SICKLE CELL/ 1000 | PERIPHERAL ERYTROBLAST IN 100 CELLS |
|---|---|---|---|---|---|---|---|---|---|
| 09 | 3,160,000 | 9.2 | 28 | 93 | 31 | 33 | 16 | 20 | 01 |
| 10 | 3,260,000 | 8.3 | 29 | 90 | 26 | 30 | 14 | 60 | 03 |
| 11 | 3,240,000 | 9.3 | 28 | 93 | 31 | 33 | 17 | 55 | 01 |
| 12 | 3,250,000 | 9.4 | 28 | 94 | 31 | 33 | 10 | 20 | 00 |
| 13 | 3,160,000 | 8.7 | 29 | 93 | 28 | 30 | 09 | 50 | 02 |
| 14 | 3,060,000 | 9.2 | 28 | 93 | 31 | 33 | 17 | 55 | 01 |
| 15 | 3,200,000 | 9.5 | 29 | 90 | 32 | 32 | 06 | 40 | 01 |

TABLE 4

| CASE NO. | ERYTROCYTES mm³ | HB g/dL | HT % | MCV fL | MCH pg | MCHC g/dL | RETICULOCYTES % | SICKLE CELL/ 1000 | PERIPHERAL ERYTROBLAST IN 100 CELLS |
|---|---|---|---|---|---|---|---|---|---|
| 01 | 2,560,000 | 7.0 | 22 | 88 | 28 | 31 | 16 | 160 | 08 |
| 02 | 2,510,000 | 7.1 | 23 | 92 | 28 | 30 | 12 | 90 | 08 |
| 03 | 3,100,000 | 7.3 | 28 | 90 | 23 | 26 | 07 | 110 | 06 |
| 04 | 3,700,000 | 7.5 | 29 | 78 | 20 | 25 | 05 | 70 | 03 |
| 05 | 3,300,000 | 8.4 | 30 | 90 | 25 | 28 | 10 | 90 | 02 |
| 06 | 2,770,000 | 8.2 | 29 | 104 | 30 | 28 | 10 | 86 | 03 |
| 07 | 2,640,000 | 8.0 | 28 | 106 | 30 | 28 | 12 | 100 | 04 |
| 08 | 2,750,000 | 8.1 | 28 | 102 | 30 | 28 | 07 | 110 | 03 |
| 09 | 2,950,000 | 9.2 | 26 | 89 | 31 | 35 | 16 | 90 | 00 |
| 10 | 3,000,000 | 9.0 | 25 | 83 | 30 | 36 | 13 | 80 | 01 |
| 11 | 2,750,000 | 8.5 | 25 | 92 | 31 | 34 | 10 | 100 | 06 |
| 12 | 2,670,000 | 8.2 | 25 | 96 | 31 | 32 | 11 | 110 | 02 |
| 13 | 2,250,000 | 7.0 | 20 | 90 | 31 | 35 | 12 | 140 | 06 |
| 14 | 3,400,000 | 8.8 | 30 | 88 | 25 | 29 | 18 | 100 | 04 |
| 15 | 3,000,000 | 8.5 | 29 | 96 | 28 | 29 | 16 | 100 | 03 |

TABLE 5

| CASE NO. | ERYTROCYTES mm³ | HB g/dL | HT % | MCV fL | MCH pg | MCHC g/dL | RETICULOCYTES % | SICKLE CELL/ 1000 | PERIPHERAL ERYTROBLAST IN 100 CELLS |
|---|---|---|---|---|---|---|---|---|---|
| 01 | 3,550,000 | 11.2 | 34 | 95 | 31 | 33 | 10 | 80 | 00 |
| 02 | 2,400,000 | 7.5 | 22 | 91 | 31 | 34 | 04 | 100 | 03 |
| 03 | 3,250,000 | 9.2 | 29 | 89 | 28 | 31 | 06 | 40 | 05 |
| 04 | 2,390,000 | 8.2 | 26 | 108 | 34 | 31 | 09 | 80 | 01 |
| 05 | 2,610,000 | 8.7 | 27 | 103 | 33 | 32 | 06 | 90 | 02 |
| 06 | 3,250,000 | 10.0 | 29 | 89 | 30 | 34 | 05 | 50 | 01 |
| 07 | 3,310,000 | 9.5 | 30 | 90 | 28 | 31 | 08 | 20 | 02 |
| 08 | 3,110,000 | 9.4 | 29 | 93 | 30 | 32 | 06 | 50 | 01 |
| 09 | 2,980,000 | 9.5 | 26 | 87 | 31 | 36 | 08 | 15 | 01 |
| 10 | 3,350,100 | 8.5 | 29 | 86 | 25 | 29 | 14 | 50 | 03 |
| 11 | 3,350,000 | 9.5 | 29 | 86 | 28 | 32 | 10 | 30 | 00 |
| 12 | 3,100,000 | 8.5 | 27 | 87 | 27 | 31 | 08 | 60 | 02 |
| 13 | 3,350,000 | 9.0 | 30 | 89 | 26 | 30 | 09 | 40 | 01 |
| 14 | 3,160,000 | 9.5 | 28 | 88 | 30 | 33 | 10 | 30 | 01 |
| 15 | 3,310,000 | 9.7 | 30 | 90 | 29 | 32 | 04 | 35 | 01 |

TABLE 6

| CASE NO. | ERYTROCYTES mm³ | HB g/dL | HT % | MCV fL | MCH pg | MCHC g/dL | RETICULOCYTES % | SICKLE CELL/ 1000 | PERIPHERAL ERYTROBLAST IN 100 CELLS |
|---|---|---|---|---|---|---|---|---|---|
| 01 | 2,850,000 | 8.0 | 26 | 91 | 28 | 30 | 06 | 30 | 02 |
| 02 | 2,350,000 | 7.1 | 21 | 89 | 30 | 33 | 12 | 90 | 06 |
| 03 | 3,050,000 | 7.2 | 27 | 88 | 23 | 26 | 10 | 110 | 07 |
| 04 | 3,000,000 | 7.9 | 25 | 83 | 26 | 32 | 03 | 15 | 01 |
| 05 | 2,800,000 | 6.6 | 22 | 79 | 24 | 30 | 20 | 150 | 02 |
| 06 | 2,830,000 | 7.0 | 20 | 70 | 24 | 35 | 10 | 100 | 06 |
| 07 | 2,730,000 | 8.1 | 28 | 102 | 29 | 28 | 13 | 120 | 04 |
| 08 | 2,790,000 | 8.0 | 28 | 100 | 28 | 28 | 07 | 100 | 03 |
| 09 | 2,980,000 | 9.3 | 26 | 87 | 31 | 35 | 15 | 90 | 00 |
| 10 | 2,750,000 | 8.5 | 24 | 87 | 30 | 35 | 13 | 100 | 02 |
| 11 | 2,520,000 | 8.0 | 25 | 99 | 31 | 32 | 09 | 120 | 07 |
| 12 | 2,570,000 | 8.1 | 23 | 89 | 31 | 35 | 11 | 120 | 02 |
| 13 | 2,150,000 | 6.8 | 19 | 88 | 31 | 35 | 18 | 166 | 08 |
| 14 | 3,510,000 | 8.7 | 29 | 82 | 24 | 30 | 14 | 110 | 04 |
| 15 | 3,110,000 | 9.3 | 28 | 90 | 29 | 33 | 07 | 50 | 01 |

Having set forth the general nature and studies of the invention, the scope is now more particularly set forth in the appended claims.

I claim:

1. A method for treating sickle cell symptomatology, said method comprising administering to a sickle cell subject a therapeutically-effective amount of an alcoholic extract of the root of the Brazilian ginseng plant.

2. The method of claim 1, wherein said alcoholic extract is in the form of a powder.

3. The method of claim 1, wherein said Brazilian ginseng plant is *Pfaffia paniculata*.

4. The method of claim 1, wherein said alcoholic extract is selected from the group consisting of Pfaffic acid, alkyl Pfaffic acid and acyl Pfaffic acid.

5. The method of claim 1, wherein said alcoholic extract is selected from the group consisting of pfaffosides and saponins.

* * * * *